United States Patent
Viola

(10) Patent No.: US 8,292,148 B2
(45) Date of Patent: *Oct. 23, 2012

(54) ARTICULATION AND FIRING FORCE MECHANISMS

(75) Inventor: Frank J. Viola, Sandy Hook, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/095,560

(22) Filed: Apr. 27, 2011

(65) Prior Publication Data
US 2011/0198386 A1 Aug. 18, 2011

Related U.S. Application Data

(63) Continuation of application No. 12/261,283, filed on Oct. 30, 2008, now Pat. No. 7,954,685.

(60) Provisional application No. 60/985,663, filed on Nov. 6, 2007.

(51) Int. Cl.
*A61B 17/068* (2006.01)
(52) U.S. Cl. ...................... 227/175.1; 227/19
(58) Field of Classification Search ............ 227/19, 227/176.1, 175.1, 178.1, 180.1; 606/139, 606/219
See application file for complete search history.

(56) References Cited

U.S. PATENT DOCUMENTS

| | | |
|---|---|---|
| 3,079,606 A | 3/1963 | Bobrov et al. |
| 3,490,675 A | 1/1970 | Green et al. |
| 3,777,538 A | 12/1973 | Weatherly et al. |
| 3,882,854 A | 5/1975 | Hulka et al. |
| 4,027,510 A | 6/1977 | Hiltebrandt |
| 4,086,926 A | 5/1978 | Green et al. |
| 4,244,372 A | 1/1981 | Kapitanov et al. |
| 4,429,695 A | 2/1984 | Green |
| 4,505,414 A | 3/1985 | Filipi |
| 4,589,413 A | 5/1986 | Malyshev et al. |
| 4,602,634 A | 7/1986 | Barkley |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |

(Continued)

FOREIGN PATENT DOCUMENTS

AU 5476586 9/1986

(Continued)

OTHER PUBLICATIONS

European Search Report for corresponding EP 08253619.4-1526 application, date of completion is Apr. 29, 2009 (4 pages).

*Primary Examiner* — Scott A. Smith

(57) ABSTRACT

There is provided a surgical instrument incorporating driving force mechanisms capable of transmitting a driving force through an articulated section of the surgical instrument. In one embodiment, a series of racks connect with a transfer gear to pass forces around the articulated section. In an alternative embodiment a series of cable sections and wheels or pulleys are provided to transmit a driving force through the articulated section of the surgical instrument.

20 Claims, 10 Drawing Sheets

U.S. PATENT DOCUMENTS

| | | |
|---|---|---|
| 4,784,137 A | 11/1988 | Kulik et al. |
| 4,863,088 A | 9/1989 | Redmond et al. |
| 4,892,244 A | 1/1990 | Fox et al. |
| 4,978,049 A | 12/1990 | Green |
| 4,991,764 A | 2/1991 | Mericle |
| 5,040,715 A | 8/1991 | Green et al. |
| 5,065,929 A | 11/1991 | Schulze et al. |
| 5,074,454 A | 12/1991 | Peters |
| 5,083,695 A | 1/1992 | Foslien et al. |
| 5,084,057 A | 1/1992 | Green et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,170,925 A | 12/1992 | Madden et al. |
| 5,171,247 A | 12/1992 | Hughetti et al. |
| 5,246,156 A | 9/1993 | Rothfuss et al. |
| RE34,519 E | 1/1994 | Fox et al. |
| 5,282,807 A | 2/1994 | Knoepfler |
| 5,307,976 A | 5/1994 | Olson et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,332,142 A | 7/1994 | Robinson et al. |
| 5,336,232 A | 8/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,376,095 A | 12/1994 | Ortiz |
| 5,381,943 A | 1/1995 | Allen et al. |
| 5,382,255 A | 1/1995 | Castro et al. |
| 5,383,880 A | 1/1995 | Hooven |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,407,293 A | 4/1995 | Crainich |
| 5,413,268 A | 5/1995 | Green et al. |
| 5,415,334 A | 5/1995 | Williamson, IV et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,497,933 A | 3/1996 | DeFonzo et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,543 A | 11/1996 | Akopov et al. |
| 5,575,799 A | 11/1996 | Bolanos et al. |
| 5,577,654 A | 11/1996 | Bishop |
| 5,579,107 A | 11/1996 | Wright et al. |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,690,269 A | 11/1997 | Bolanos et al. |
| 5,692,668 A | 12/1997 | Schulze et al. |
| 5,697,542 A | 12/1997 | Knodel et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,716,366 A | 2/1998 | Yates |
| 5,725,536 A | 3/1998 | Oberlin et al. |
| 5,725,554 A | 3/1998 | Simon et al. |
| 5,728,110 A | 3/1998 | Vidal et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |

| | | | |
|---|---|---|---|
| 5,782,396 A | 7/1998 | Mastri et al. |
| 5,782,397 A | 7/1998 | Koukline |
| 5,782,834 A | 7/1998 | Lucey et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson, IV et al. |
| 5,873,873 A | 2/1999 | Smith et al. |
| 5,897,562 A | 4/1999 | Bolanos et al. |
| 5,901,895 A | 5/1999 | Heaton et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,954,259 A | 9/1999 | Viola et al. |
| 5,980,510 A | 11/1999 | Tsonton et al. |
| 6,004,335 A | 12/1999 | Vaitekunas et al. |
| 6,010,054 A | 1/2000 | Johnson et al. |
| 6,032,849 A | 3/2000 | Mastri et al. |
| 6,079,606 A | 6/2000 | Milliman et al. |
| 6,109,500 A | 8/2000 | Alli et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,269,977 B1 | 8/2001 | Moore |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,436,097 B1 | 8/2002 | Nardella |
| 6,439,446 B1 | 8/2002 | Perry et al. |
| 6,443,973 B1 | 9/2002 | Whitman |
| 6,463,623 B2 | 10/2002 | Ahn et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,612,053 B2 | 9/2003 | Liao |
| 6,619,529 B2 | 9/2003 | Green et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,731,473 B2 | 5/2004 | Li et al. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,808,262 B2 | 10/2004 | Chapoy et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,879,880 B2 | 4/2005 | Nowlin et al. |
| 6,889,116 B2 | 5/2005 | Jinno |
| 6,905,057 B2 | 6/2005 | Swayze et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,731 B2 | 6/2006 | Shelton, IV et al. |
| 7,059,508 B2 | 6/2006 | Shelton, IV et al. |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,128,253 B2 | 10/2006 | Mastri et al. |
| 7,128,254 B2 | 10/2006 | Shelton, IV et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,147,138 B2 | 12/2006 | Shelton, IV |
| 7,159,750 B2 | 1/2007 | Racenet et al. |
| 7,278,563 B1 | 10/2007 | Green |
| 7,328,828 B2 | 2/2008 | Ortiz et al. |
| 7,404,508 B2 | 7/2008 | Smith et al. |
| 7,419,080 B2 | 9/2008 | Smith et al. |
| 7,448,525 B2 | 11/2008 | Shelton et al. |
| 7,455,208 B2 | 11/2008 | Wales et al. |
| 7,464,849 B2 | 12/2008 | Shelton et al. |
| 7,543,731 B2 | 6/2009 | Green et al. |
| 7,559,450 B2 | 7/2009 | Wales et al. |
| 7,588,176 B2 | 9/2009 | Timm et al. |
| 7,654,431 B2 | 2/2010 | Hueil et al. |
| 7,770,775 B2 | 8/2010 | Shelton et al. |
| 7,954,685 B2 * | 6/2011 | Viola .................. 227/175.1 |
| 2002/0004498 A1 | 1/2002 | Doherty |
| 2002/0009193 A1 | 1/2002 | Deguchi |
| 2002/0018323 A1 | 2/2002 | Li |
| 2002/0032948 A1 | 3/2002 | Ahn |
| 2002/0036748 A1 | 3/2002 | Chapoy |
| 2002/0045442 A1 | 4/2002 | Silen et al. |
| 2002/0069595 A1 | 6/2002 | Knudson et al. |
| 2002/0084304 A1 | 7/2002 | Whitman |
| 2002/0111621 A1 | 8/2002 | Wallace et al. |
| 2002/0143346 A1 | 10/2002 | McGuckin, Jr. et al. |
| 2002/0177843 A1 | 11/2002 | Anderson et al. |
| 2002/0188294 A1 | 12/2002 | Couture et al. |
| 2002/0190093 A1 | 12/2002 | Fenton, Jr. |
| 2003/0009193 A1 | 1/2003 | Corsaro |
| 2003/0105476 A1 | 6/2003 | Sancoff et al. |
| 2003/0132268 A1 | 7/2003 | Whitman |
| 2004/0004105 A1 | 1/2004 | Jankowski |
| 2004/0007608 A1 | 1/2004 | Ehrenfels et al. |
| 2004/0050902 A1 | 3/2004 | Green |
| 2004/0093029 A1 | 5/2004 | Zubik et al. |
| 2004/0094597 A1 | 5/2004 | Whitman |
| 2004/0108357 A1 | 6/2004 | Milliman |
| 2004/0149802 A1 | 8/2004 | Whitman |
| 2004/0173659 A1 | 9/2004 | Green |
| 2004/0199181 A1 | 10/2004 | Knodel et al. |
| 2004/0232199 A1 | 11/2004 | Shelton, IV et al. |
| 2004/0232200 A1 | 11/2004 | Shelton, IV et al. |
| 2004/0232201 A1 | 11/2004 | Wenchell |
| 2004/0243151 A1 | 12/2004 | Demmy |
| 2004/0267310 A1 | 12/2004 | Racenet |
| 2005/0006429 A1 | 1/2005 | Wales |
| 2005/0006430 A1 | 1/2005 | Wales |
| 2005/0006431 A1 | 1/2005 | Shelton, IV et al. |
| 2005/0006432 A1 | 1/2005 | Racenet |
| 2005/0006433 A1 | 1/2005 | Milliman |
| 2005/0006434 A1 | 1/2005 | Wales et al. |

| | | | |
|---|---|---|---|
| 2005/0023324 A1 | 2/2005 | Doll et al. | |
| 2005/0023325 A1 | 2/2005 | Gresham | |
| 2005/0067457 A1 | 3/2005 | Shelton | |
| 2005/0067458 A1 | 3/2005 | Swayze et al. | |
| 2005/0067459 A1 | 3/2005 | Swayze et al. | |
| 2005/0067460 A1 | 3/2005 | Milliman | |
| 2005/0072827 A1 | 4/2005 | Mollenauer | |
| 2005/0103819 A1 | 5/2005 | Racenet | |
| 2005/0119669 A1 | 6/2005 | Demmy | |
| 2005/0127131 A1 | 6/2005 | Mastri | |
| 2005/0165415 A1 | 7/2005 | Wales | |
| 2005/0173490 A1 | 8/2005 | Shelton, IV | |
| 2005/0178813 A1 | 8/2005 | Swayze et al. | |
| 2005/0184123 A1 | 8/2005 | Scirica et al. | |
| 2005/0184124 A1 | 8/2005 | Scirica et al. | |
| 2005/0184125 A1 | 8/2005 | Marczyk | |
| 2005/0184126 A1 | 8/2005 | Green et al. | |
| 2005/0189397 A1 | 9/2005 | Jankowski | |
| 2005/0216055 A1 | 9/2005 | Scirica et al. | |
| 2005/0263562 A1 | 12/2005 | Shelton, IV et al. | |
| 2005/0279804 A1 | 12/2005 | Scirica et al. | |
| 2006/0000867 A1 | 1/2006 | Shelton, IV et al. | |
| 2006/0000868 A1 | 1/2006 | Shelton, IV et al. | |
| 2006/0011699 A1 | 1/2006 | Olson et al. | |
| 2006/0016853 A1 | 1/2006 | Racenet | |
| 2006/0022014 A1 | 2/2006 | Shelton, IV et al. | |
| 2006/0022015 A1 | 2/2006 | Shelton, IV et al. | |
| 2006/0049230 A1 | 3/2006 | Shelton, IV et al. | |
| 2006/0069396 A1 | 3/2006 | Meade et al. | |
| 2006/0124688 A1 | 6/2006 | Racenet et al. | |
| 2006/0151567 A1 | 7/2006 | Roy | |
| 2006/0151568 A1 | 7/2006 | Weller et al. | |
| 2006/0175375 A1 | 8/2006 | Shelton, IV et al. | |
| 2006/0180634 A1 | 8/2006 | Shelton, IV et al. | |
| 2006/0190034 A1 | 8/2006 | Nishizawa et al. | |
| 2006/0201990 A1 | 9/2006 | Mastri et al. | |
| 2006/0201991 A1 | 9/2006 | Mastri et al. | |
| 2006/0226195 A1 | 10/2006 | Scirica et al. | |
| 2006/0226196 A1 | 10/2006 | Hueil et al. | |
| 2006/0278680 A1 | 12/2006 | Viola et al. | |
| 2006/0278681 A1 | 12/2006 | Viola et al. | |
| 2006/0289600 A1 | 12/2006 | Wales et al. | |
| 2006/0289602 A1 | 12/2006 | Wales et al. | |
| 2007/0023477 A1 | 2/2007 | Whitman et al. | |
| 2007/0102472 A1 | 5/2007 | Shelton, IV | |
| 2007/0102473 A1 | 5/2007 | Shelton, IV | |
| 2007/0102474 A1 | 5/2007 | Shelton, IV | |
| 2007/0102476 A1 | 5/2007 | Shelton, IV | |
| 2007/0106317 A1 | 5/2007 | Shelton, IV | |

FOREIGN PATENT DOCUMENTS

| | | |
|---|---|---|
| DE | 2744824 | 4/1978 |
| DE | 2903159 | 1/1980 |
| DE | 3114135 | 10/1982 |
| DE | 4213426 | 10/1992 |
| DE | 4300307 | 7/1994 |
| EP | 0041022 | 12/1981 |
| EP | 0136950 | 4/1985 |
| EP | 0140552 | 5/1985 |
| EP | 0156774 | 10/1985 |
| EP | 0216532 | 4/1987 |
| EP | 0220029 | 4/1987 |
| EP | 0213817 | 11/1987 |
| EP | 0273468 | 7/1988 |
| EP | 0324166 | 7/1989 |
| EP | 0324635 | 7/1989 |
| EP | 0324637 | 7/1989 |
| EP | 0324638 | 7/1989 |
| EP | 0369324 | 5/1990 |
| EP | 0373762 | 6/1990 |
| EP | 0380025 | 8/1990 |
| EP | 0399701 | 11/1990 |
| EP | 0449394 | 10/1991 |
| EP | 0484677 | 5/1992 |
| EP | 0489436 | 6/1992 |
| EP | 0503662 | 9/1992 |
| EP | 0514139 | 11/1992 |
| EP | 0536903 | 4/1993 |
| EP | 0537572 | 4/1993 |
| EP | 0539762 | 5/1993 |
| EP | 0545029 | 6/1993 |
| EP | 0552050 | 7/1993 |
| EP | 0552423 | 7/1993 |
| EP | 0579038 | 1/1994 |
| EP | 0589306 | 3/1994 |
| EP | 0591946 | 4/1994 |
| EP | 0592243 | 4/1994 |
| EP | 0593920 | 4/1994 |
| EP | 0598202 | 5/1994 |
| EP | 0598579 | 5/1994 |
| EP | 0621006 | 10/1994 |
| EP | 0621009 | 10/1994 |
| EP | 0656188 | 6/1995 |
| EP | 0365153 | 8/1995 |
| EP | 0666057 | 8/1995 |
| EP | 0705571 | 4/1996 |
| EP | 0760230 | 3/1997 |
| EP | 1813203 A | 8/2007 |
| FR | 2542188 | 9/1984 |
| FR | 2660851 | 10/1991 |
| FR | 2681775 | 10/1991 |
| GB | 1352554 | 4/1971 |
| GB | 1452185 | 10/1976 |
| GB | 1555455 | 11/1979 |
| GB | 2048685 | 12/1980 |
| GB | 2070499 | 9/1981 |
| GB | 2141066 | 12/1984 |
| GB | 2165559 | 4/1986 |
| JP | 51-149985 | 5/1975 |
| SU | 728848 | 5/1977 |
| SU | 659146 | 4/1979 |
| SU | 980703 | 12/1982 |
| SU | 990220 | 1/1983 |
| WO | WO8302247 | 7/1983 |
| WO | WO 89/10094 | 11/1989 |
| WO | WO9210976 | 7/1992 |
| WO | 9308754 | 5/1993 |
| WO | 9314706 | 8/1993 |

* cited by examiner

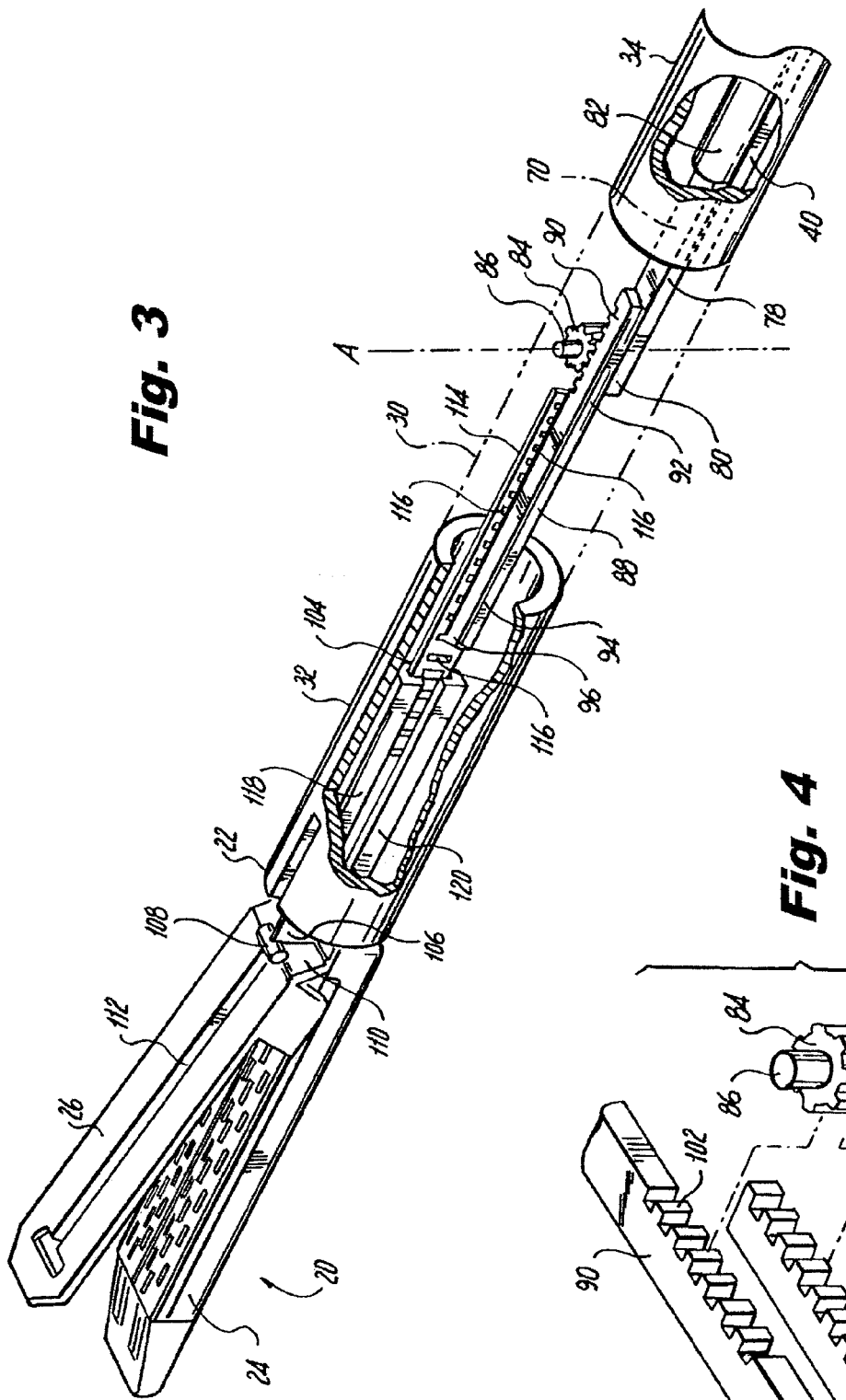

ARTICULATION AND FIRING FORCE MECHANISMS

CROSS-REFERENCE TO RELATED APPLICATIONS

This application is a continuation of U.S. application Ser. No. 12/261,283 filed Oct. 30, 2008, now U.S. Pat. No. 7,954, 685 which claims the benefit of and priority to U.S. Provisional Application Ser. No. 60/985,663, filed on Nov. 6, 2007, the entire contents of each of which are incorporated herein by reference.

BACKGROUND

1. Technical Field

The present disclosure relates to firing force mechanisms for use in a surgical instrument. More particularly, the present disclosure relates to firing force mechanisms capable of transmitting a firing or driving force around an angle within a surgical stapling instrument.

2. Background of Related Art

Various surgical instruments are known in the art for performing operations within a body cavity. Certain of these instruments are configured to pass through an access opening in the body of the patient. A handle portion of the instrument remains outside the body while an elongate portion of the instrument passes through the port and into the body cavity. When these types of devices are utilized, it is often difficult to orient the distal end of the elongate portion within body by manipulation of the handle portion of the instrument from outside of the body.

Unique instruments have been developed which allow the elongate portion of the instrument entering the body to bend or move within the body independent of the position of the handle portion of the instrument outside the body. These "articulating" surgical instruments employ various mechanisms to cause the elongate portion to bend or be reoriented within the body.

While it is relatively easy for the elongate portion of instrument to be bent or reoriented within the body, the ability to transmit an actuation or driving force around the bend to an end effector associated with the elongate portion poses difficulties. These difficulties include loss of force due to bowing or flexing of the drive elements as they pass around the bend in the elongate portion, etc.

SUMMARY

There is provided a surgical instrument including a handle having an elongate tubular member extending distally from the handle. The elongate tubular member has a proximal portion, a distal portion and an articulation section positioned between the distal and proximal portions. The articulation section allows the distal portion to move relative to the proximal section.

A drive force mechanism is provided in the surgical instrument and includes a drive element positioned in the proximal portion, a transfer bar positioned in the distal portion and a transfer device positioned in the articulation section. The transfer device receives a driving force from the drive element and reorients the driving force around the articulation section and toward the transfer bar. The transfer device is rotatably mounted in the articulation section.

The transfer device is rotatably mounted in the articulation section. In one embodiment, the drive element is a gear rotatably mounted at a point of articulation. The drive element includes a rack engagable with the gear so as to rotate the gear in response to longitudinal motion of the rack. The transfer bar includes a rack engagable with the gear such that rotation of the gear moves the transfer bar longitudinally within the distal portion.

In an alternative embodiment the transfer device includes at least one wheel rotatably mounted in the articulation section. The drive element is a flexible cable which passes around the at least one wheel. The drive mechanism includes a toggle rotatably mounted in the distal portion, a first end of the toggle being connected to the transfer bar. A second end of the toggle is connected to the cable. The cable has an upper section and a lower section, the upper section being connected to the first end of the toggle and the lower section being connected to the second end of the toggle.

The surgical instrument further includes an actuator positioned in the distal portion to operate an end effector associated with the surgical instrument. The transfer bar is engagable with the actuator and includes a drive tooth engagable with the actuator.

In a specific embodiment, the drive tooth is releasably engagable with the actuator. The actuator includes a plurality of abutments and the drive tooth includes a drive face engagble within the abutments. The drive tooth also includes a proximal sloped face, the proximal sloped face is engagable with the abutments to disengage the drive tooth from the abutments.

DESCRIPTION OF THE DRAWINGS

Various embodiments of the presently driving force mechanisms are disclosed herein with reference to the drawings, wherein:

FIG. 3 is an enlarged perspective view, partially shown in section, of a distal end portion of the surgical stapler of FIG. 1, in a non-articulated position;

FIG. 4 is a perspective view of force transferring components of the surgical instrument of FIG. 1;

DETAILED DESCRIPTION OF EMBODIMENTS

Embodiments of the presently disclosed driving force mechanisms for use in surgical instruments will now be described in detail with reference to the drawings wherein like numerals designate identical or corresponding elements in each of the several views. As is common in the art, the term "proximal" refers to that part or component closer to the user or operator, i.e. user, surgeon or physician, while the term "distal" refers to that part or component further away from the user.

Figure 1:
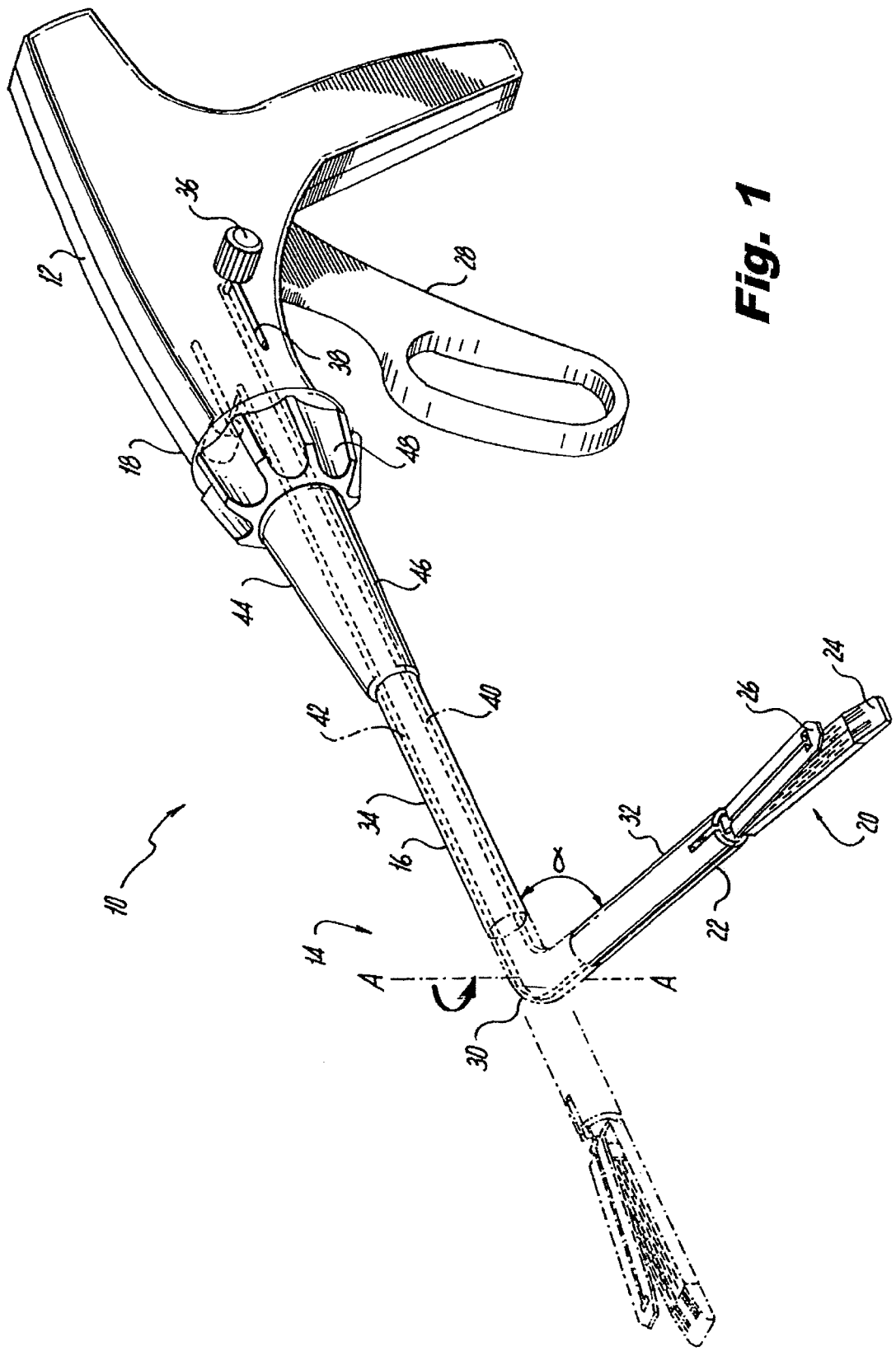
FIG. 1 is a perspective view of an articulating surgical stapler incorporating a first embodiment of a driving force mechanism.

FIG. 1 illustrates a surgical stapler 10 incorporating one embodiment of a driving force mechanism. Surgical stapler 10 generally includes a handle 12 and a distal end portion 14 extending distally from handle 12. Distal end portion 14 is configured for endoscopic use and includes an elongate tubular member 16 extending from a distal end 18 of handle 12. A jaw assembly 20 is mounted on a distal end 22 of elongate tubular member 16 and includes a staple cartridge 24 and an anvil 26. Anvil 26 is mounted for movement between an open position spaced apart from staple cartridge to a closed position substantially adjacent staple cartridge 24. A trigger 28 is provided on handle 12 to actuate jaw assembly 20.

Surgical stapler 10 is of the type of surgical instruments that are capable of bending or articulating about an articulation section 30 in elongate tubular member 16. Articulation section 30 is located about midway along elongate tubular member 16 separating elongate tubular member 16 into a distal portion 32 and a proximal portion 34. Elongate tubular member 16 bends about an axis "A" of articulation section 30 through an angle α. An articulation actuator 36 is provided on handle 12 to move distal portion 32 relative to proximal portion 34 about axis A (shown in FIGS. 1, 2). Articulation actuator 36 moves articulators 40 and 42 which extend from articulation actuator 36 to articulation section 30. (See FIG. 5) While not specifically shown, various mechanisms are known in the art which are capable of effecting angular movement of distal portion 32 of elongate tubular member 16 relative to proximal portion 34 of elongate tubular member 16 about axis A and through angle α. For example, linkages, flexible bands, gears, etc. In a particular embodiment angle α can be between about 0° to about 90° or more from the longitudinal axis of the proximal portion 34.

In order to properly orient jaw assembly 20 relative to tissue, surgical stapler 10 includes a rotation knob 44 rotatably mounted on handle 12. Elongate tubular member 16 is mounted in a nose cone portion 46 of rotation knob 44 and a knurled portion 48 is provided on rotation knob 44 to facilitate rotation of distal end portion 14 relative to handle 12.

Figure 2:
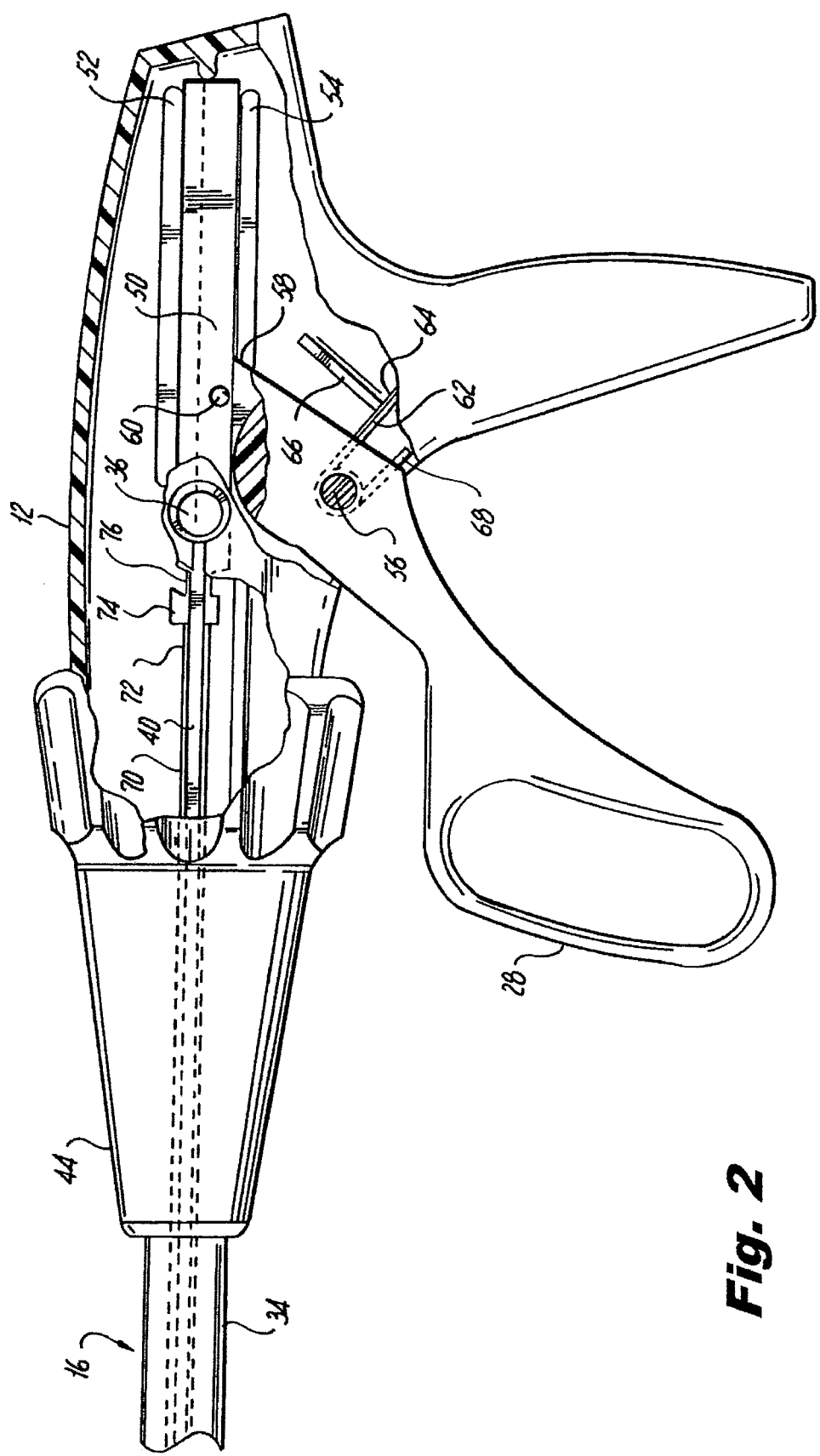
FIG. 2 is a side view, partially shown in section, of a handle assembly of the surgical stapler of FIG. 1.

Referring to FIG. 2, a driver 50 is mounted for longitudinal movement within handle 12. A pair of guide rails 52 and 54 are provided in handle to support driver 50. As noted above, trigger 28 is provided to actuate jaw assembly 20. Trigger 28 is pivotally mounted on a pivot post 56 formed in handle 20. An upper end 58 of trigger 28 is connected to driver 50 by a pivot pin 60. Movement of trigger 28 translates driver 50 within handle 12 to actuate jaw assembly 20. A return spring 62 is positioned over pivot post 56 and is engagable at a first end 64 with a projection 66 formed in handle 12. A second end 68 of guide spring 64 engages trigger 28 to bias trigger 28 to an open or unfired position.

As noted above, surgical stapler 10 includes a drive force mechanism in order to transfer an actuation force from trigger 28 to jaw assembly 20. The drive force mechanism includes a drive bar 70 provided within proximal portion 34 of elongate tubular member 16. Drive bar 70 is connected at its proximal end 72 to a rotation collar 74 rotatably mounted in handle 12. Rotation collar 74 is connected to a distal end 76 of driver 50. Rotation collar 74 is provided to allow drive rod 70, as well as other driving force mechanism components, to rotate as distal end portion 14 is rotated through manipulation of rotation knob 44.

Referring now to FIG. 3, drive rod 70 extends through proximal portion 34 to articulation section 30. A distal end 78 of drive rod 70 includes a first rack 80 to facilitate transfer of a driving force around and through articulation section 30. Drive rod 70 is routed through a guide tube 82 mounted within proximal portion 34 of elongate tubular member 16 to separate driving mechanism components from articulation components. In order to transfer a driving force through articulation section 30, a transfer device, such as transfer gear 84, is rotatably mounted within articulation section 30 on a center spindle 86. Center spindle 86 is mounted within articulation section 30 along axis A. Transfer gear 84 is engagable with drive rod 70 in a manner discussed hereinbelow. A transfer bar 88 is provided within distal portion 32 of elongate tubular member 16 and is provided to transmit forces received from drive rod 70 to jaw assembly 20. Transfer bar 88 includes a second rack 90, at a proximal end 92 thereof, which is engagable with transfer gear 84. A distal end 94 of transfer bar 88 terminates in a drive tooth 96.

Referring to FIG. 4, first rack 80 includes a plurality of first teeth 98 which are engagable with gear teeth 100 formed on transfer gear 84. Likewise, second rack 90 includes a plurality of teeth 102 also engagable with gear teeth 100 on transfer gear 84. Thus, as drive rod 70 moves longitudinally, first rack 80 rotates transfer gear 84 which in turn drives transfer bar 88 longitudinally within distal portion 32.

Referring back to FIG. 3, an actuator 104 is movably mounted within distal portion 32. A distal end 106 of actuator 104 includes a crossbar 108 which is engagable with an angled edge of anvil 26 to move anvil 26 between the open and closed positions. While not specifically shown, a knife is also associated with distal end 106 of actuator 104 to sever tissue captured between anvil 26 and staple cartridge 24. Anvil 26 includes a longitudinal slot 112 to allow passage of the knife through jaw assembly 20.

In order to receive the driving force from transfer bar 88, a proximal end 114 of actuator 104 is provided with a series of abutments 116 engagable with drive tooth 96 at distal end 94 of transfer bar 88. (See FIGS. 3 and 7) Drive tooth 96 repeatedly engages subsequent abutments 116 to incrementally advance actuator 104 within distal portion 32 and thus actuate jaw assembly 20. Actuator 104 is supported for longitudinal motion within distal portion 32 by a pair of guide channels 118 and 120. The abutments 116 may be formed as surfaces defining windows in the actuator 104, notches, pins or teeth.

The use of the disclosed driving force mechanism of surgical stapler 10 to transmit a driving force around a bend in surgical stapler will now be described. Referring initially to FIGS. 2 and 3, surgical stapler 10 is in an initial position with spring 62 biasing trigger 28 to the open or unfired position. Upper end 58 of trigger 28 places driver 50, and thus drive bar 70, in a proximal position within handle 12 (FIG. 2). As shown in FIG. 3, distal portion 32 of elongate tubular member 16 is in longitudinal alignment with proximal portion 34 and anvil 26 is in the open position spaced apart from staple cartridge 24. Transfer bar 88 and actuator 104 are also in proximal positions within distal portion 32.

Figure 5:
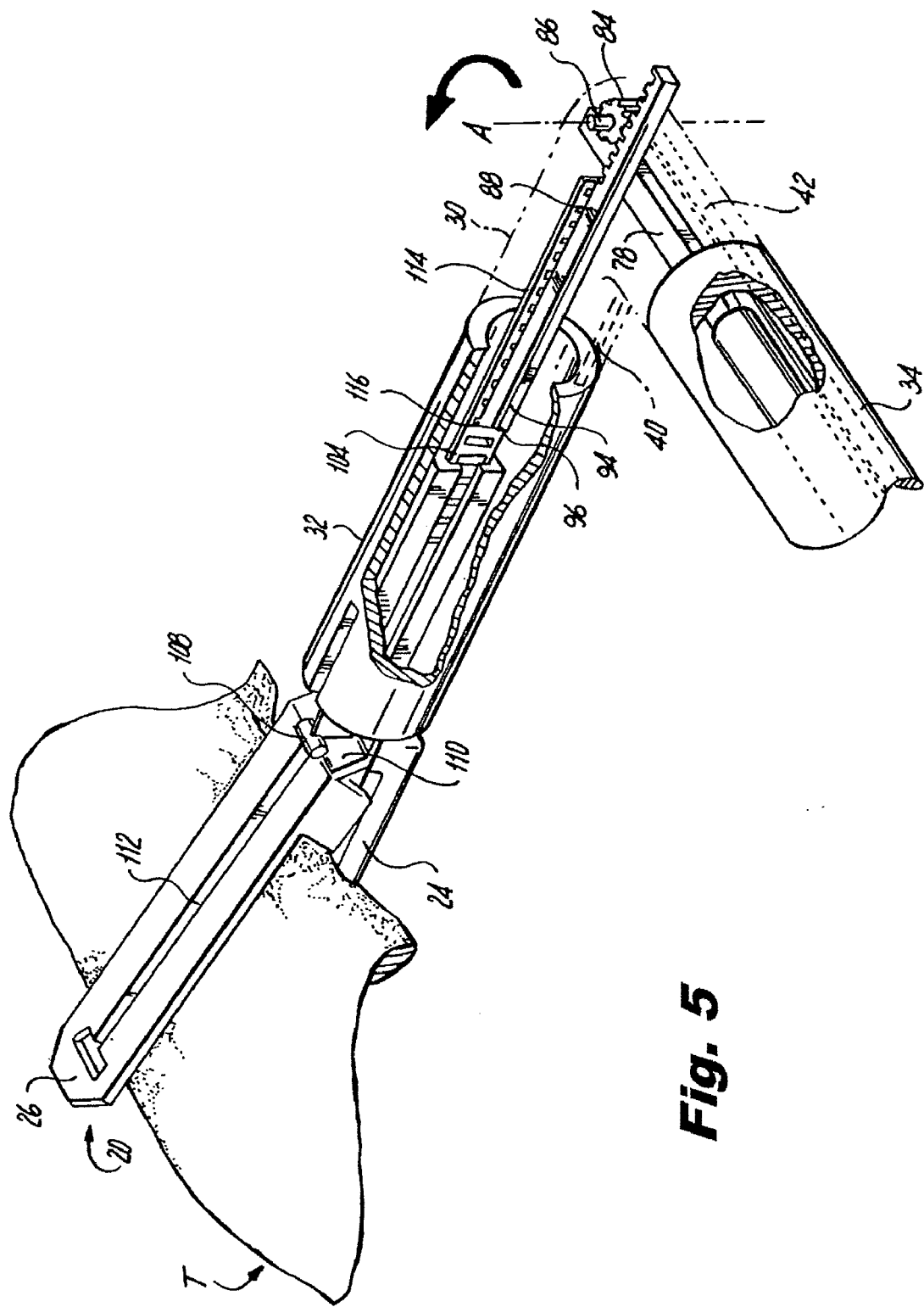
FIG. 5 is a perspective view, partially shown in section, of the distal end portion of the surgical stapler of FIG. 1 shown in an articulated position, positioned about a tissue section.

Referring now to FIGS. 1 and 5, upon actuation of articulation actuator 36 (FIG. 1), articulators 40 and 42 are activated to cause elongate tubular member 16 to bend at axis A in articulation section 30 thereby positioning distal portion 32 of elongate tubular member 16 at an angle of approximately 90° relative to proximal portion 34 (FIG. 5). As noted above, various mechanisms and methods are well known in the art to accomplish the bending or articulation at articulation section 30. Jaw assembly 16 is initially positioned about a tissue section "T" to be operated on.

Figure 6:
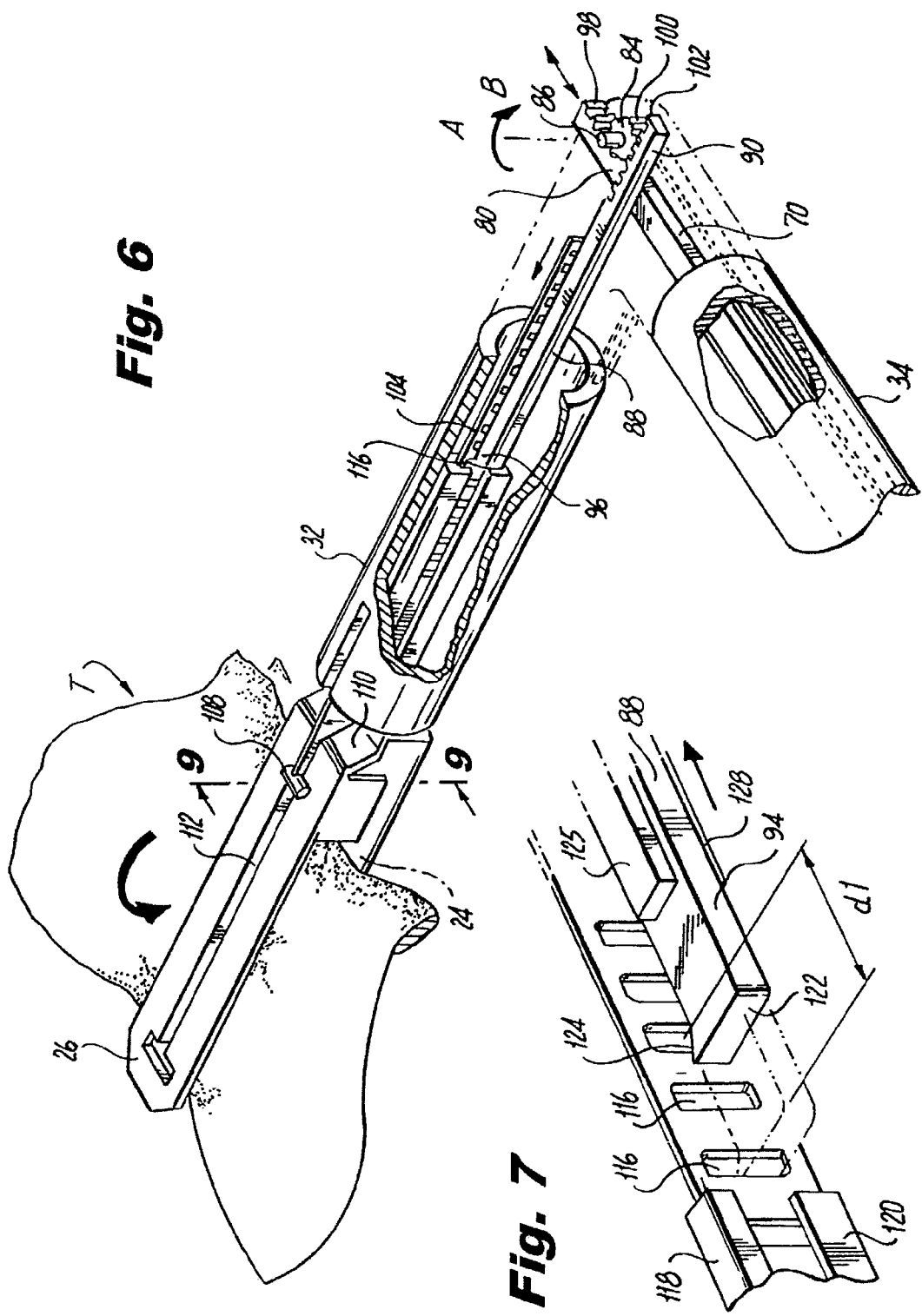
FIG. 6 is a perspective view similar to FIG. 5 during actuation of the surgical stapler.

Referring to FIGS. 1 and 6, trigger 28 is actuated or squeezed proximally causing upper end 58 to drive driver 50 distally within handle 12. As driver 50 moves distally it moves drive bar 70 distally within proximal portion 34 of elongate tubular member 16. As best shown in FIG. 6, distal movement of drive bar 70 rotates transfer gear 84 clockwise about axis A and in the direction of arrow B. Specifically, first teeth 98 of drive bar 70 engages and rotates gear teeth 100 of transfer gear 84. Transfer gear 84 receives the driving force from drive bar 70 and transfers or "redirects" the force through angle α, here 90°, to transfer bar 88. Specifically, gear teeth 10 engage second teeth 102 in second rack 90 forcing transfer bar distally within distal portion 32 of elongate tubular member 16. Thus, the combination of drive bar 70 including first rack 80, transfer gear 84 and transfer bar 88 including second rack 90 form a drive force transfer or "redirecting" mechanism allowing a drive force to be transmitted through an angle formed in a portion of surgical stapler 10. As noted above, drive force mechanisms disclosed herein are equally applicable to other surgical instruments, such as, for example, graspers, cutters, clip appliers, etc. Further, the disclosed drive force mechanisms are equally applicable in other surgical instruments having articulation sections located at other positions on the surgical instrument, for example, at the juncture of a handle and elongate tubular member, adjacent an end effector, etc.

Figure 7:
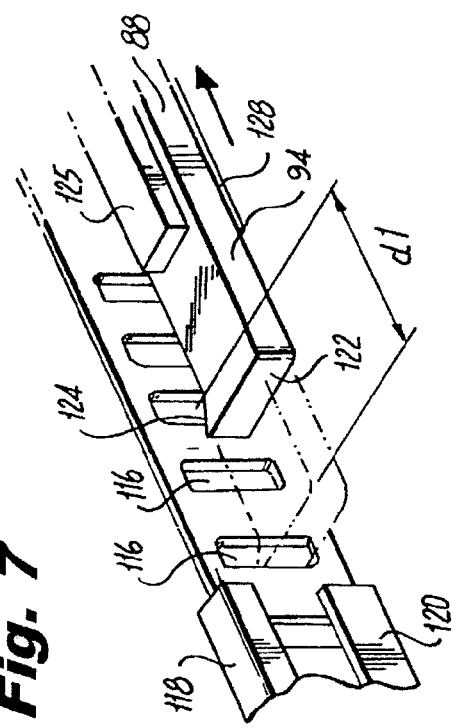
FIG. 7 is an enlarged perspective view illustrating a portion of the driving force mechanism resetting for a further actuation of the surgical stapler.

Referring to FIG. 7, as noted above, drive tooth 96 on transfer bar 88 engages sequential abutments 116 in ratchet or incremental fashion to move actuator 104 distally within distal portion 32 thereby actuating jaw assembly 20. In some cases it may be necessary to provide multiple activations of trigger 28 to fully actuate jaw assembly 20. For each activation of trigger 28, transfer bar 88 and specifically drive tooth 96 moves through a stroke length d1. Drive tooth has a distal drive face 122 to engage abutments 116. In order for transfer bar to pass through a return stroke, drive tooth 96 includes a proximal sloped face 124 which allows drive tooth 96 to disconnect from or "slip out of" abutments 116. Further activation of trigger 28 causes distal drive face 122 of drive tooth 96 to engage subsequent abutments 116. Guide rails 126 and 128 are provided within distal portion 32 to allow distal end 94 of transfer bar 88 to move laterally away from abutments 116, as well as guide transfer bar 88 in its longitudinal motion within distal portion 32.

Figure 8:
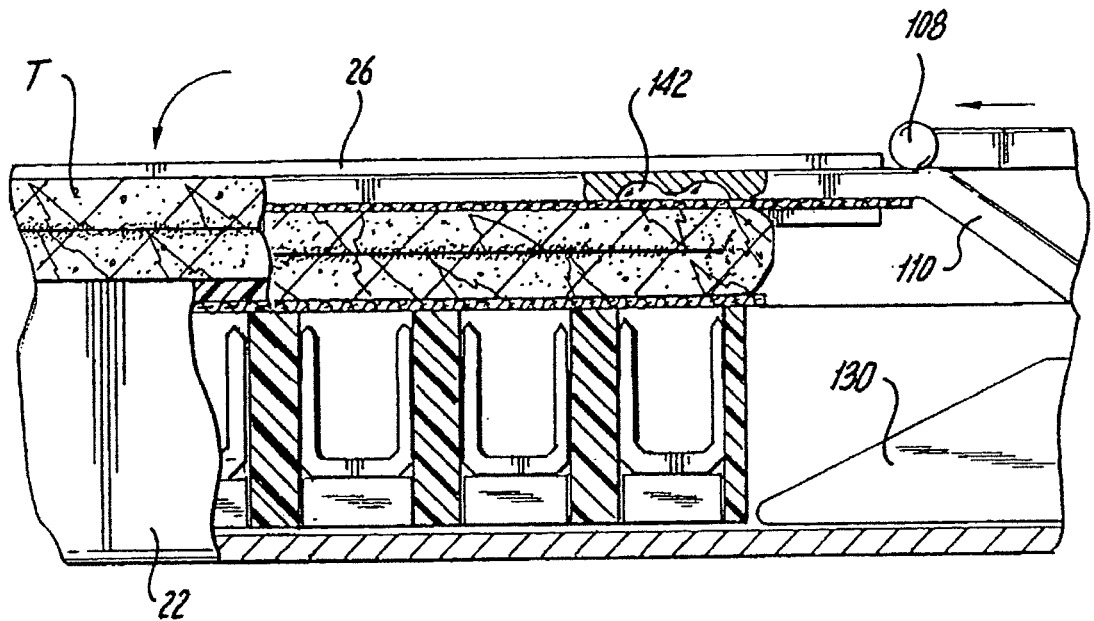
FIG. 8 is an enlarged side view, partially shown in section, of a staple cartridge and anvil of the surgical stapler during initial actuation.

Referring to FIGS. 6 and 8, upon full actuation, cross bar 108 of actuator 104 engages angled edge 110 on anvil 26 moving anvil 26 to the closed position relative to staple cartridge 24.

Figure 9:
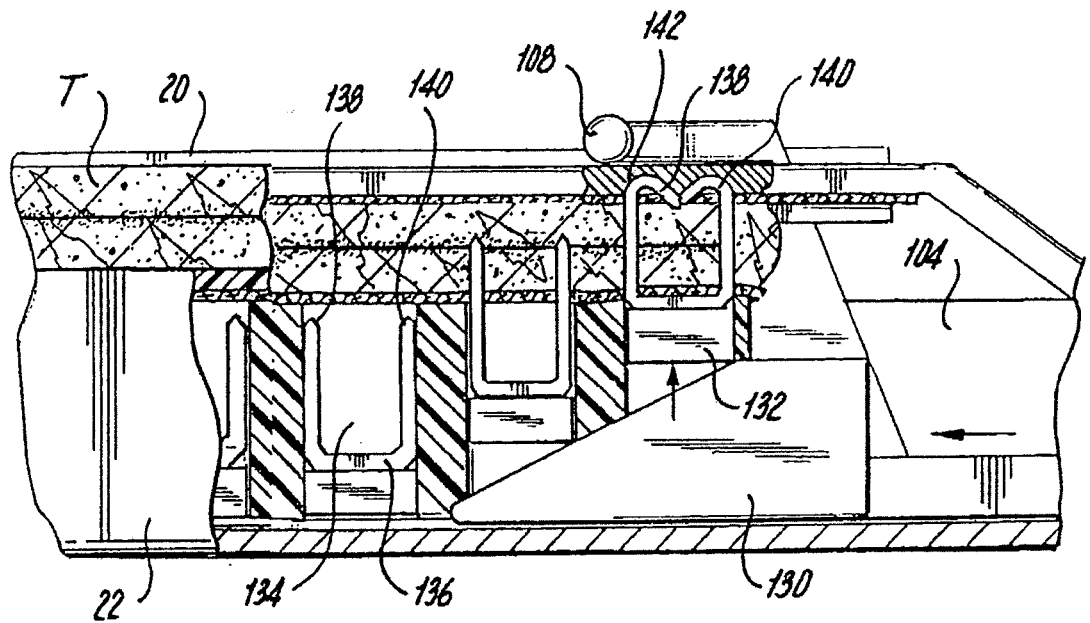
FIG. 9 is an enlarged side view, similar to FIG. 8, illustrating further actuation of the surgical stapler to staple the tissue section.

Referring now to FIG. 9, upon further actuation of surgical stapler 10, a staple bar 130 associated with actuator 104 is moved distally through staple cartridge 24 as actuator 104 moves distally through slot 112 in anvil 26. Staple bar 130 engages pushers 132 positioned within staple pockets 134 in staple cartridge 24. Pushers 132 drive staples 136, also positioned within staple pockets 134, toward anvil 26 such that pointed ends 138, 140 are driven through tissue T and into staple clinching pockets 142 in anvil 26 to thereby staple tissue section T. As noted above, a knife associated with actuator 104 moves distally with cross bar 108 to sever tissue T between the staple lines formed by staples 136.

Referring now to FIGS. 10-14, there is disclosed another embodiment of a drive force mechanism for use in surgical instruments such as surgical stapler 10. With initial reference to FIG. 10, surgical stapler 10 is as described hereinabove. However, in place of drive bars, racks and gears, the disclosed alternative embodiment includes a cable, wheel and/or pulley system to transfer a driving force from trigger 28 around and through articulation section 30 and to jaw assembly 20. Specifically, a wheel 150 is rotatably mounted on a pivot 152 in handle 12. Upper end 58 is connected to drive wheel 150 at pivot pin 60 so as to rotate drive wheel 150 in response to activation of trigger 28. A drive cable 154 passes around wheel 150 and extends through proximal portion 34 of elongate tubular member 16 and through articulation section 30 to distal portion 32 of elongate tubular member 16. Drive cable 154 is formed from a flexible material so as to pass around wheel 150. Drive cable 154 includes an upper section 156 and a lower section 158. As trigger 28 is activated, upper end 58 of trigger 12 rotates wheel 150 clockwise in handle 12 to advance upper section 156 distally and draw lower section 158 proximally within elongate tubular member 16. A collar 160 is provided within handle 12 and allows drive cable 154 to rotate as elongate tubular member 16 rotates in the manner described hereinabove.

Figure 11:
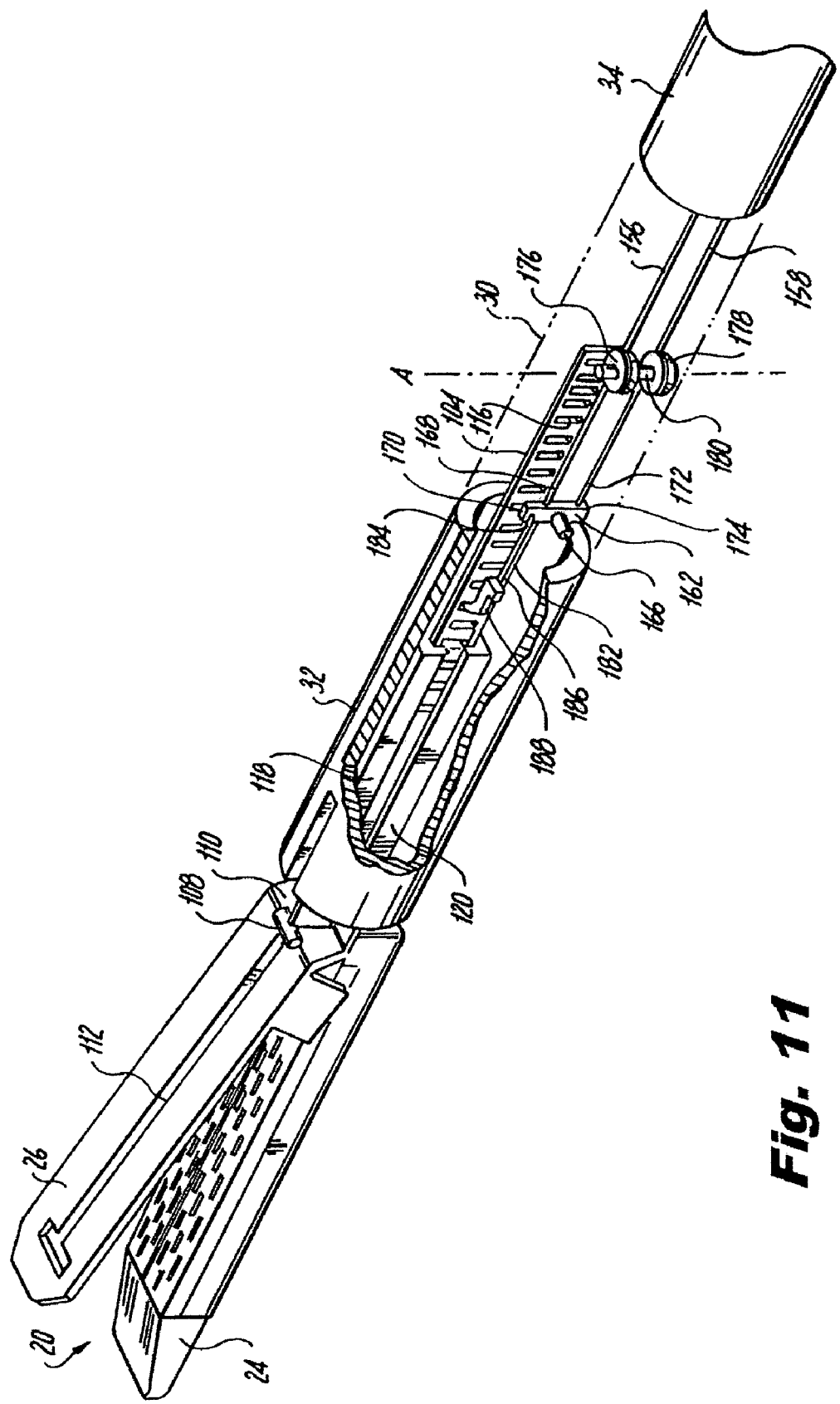
FIG. 11 is a perspective view, partially shown in section, of a distal end portion of the surgical stapler of FIG. 10, shown in a non-articulated position.

Referring to FIG. 11, in order to pass the driving forces from drive cable 154 to actuator 104, a lever 162 is provided within distal portion 32 and pivotally mounted at a pivot point 166 on a centerpost 164. A distal end 168 of upper section 156 of drive cable 154 is connected to a first end 170 of lever 162 and a distal end 172 of lower section 158 is connected to a second end 174 of lever 162.

As noted above, the disclosed drive force mechanisms incorporate transfer devices positioned within articulation section 30 of surgical stapler 10 to transfer and redirect a driving force passing though elongate tubular member 16 as elongate tubular member 16 is bent through an angle α. In this embodiment, the transfer device is in the form of a pair of wheels, including an upper wheel 176 and a lower wheel 178, rotatably mounted on a spindle 180 positioned within articulation section 30. Spindle 180 is located on axis A of surgical stapler 10.

A transfer bar 182 is positioned within distal portion 32 to transfer forces between lever 162 and actuator 104. A proximal end 184 is affixed to first end 178 of lever 162 and a distal end 186 of transfer bar 182 is attached to a drive tooth 188 which functions substantially identically to drive tooth 96, described hereinabove, to engage abutments 116 and advance actuator 104 within distal portion 32.

Figure 10:
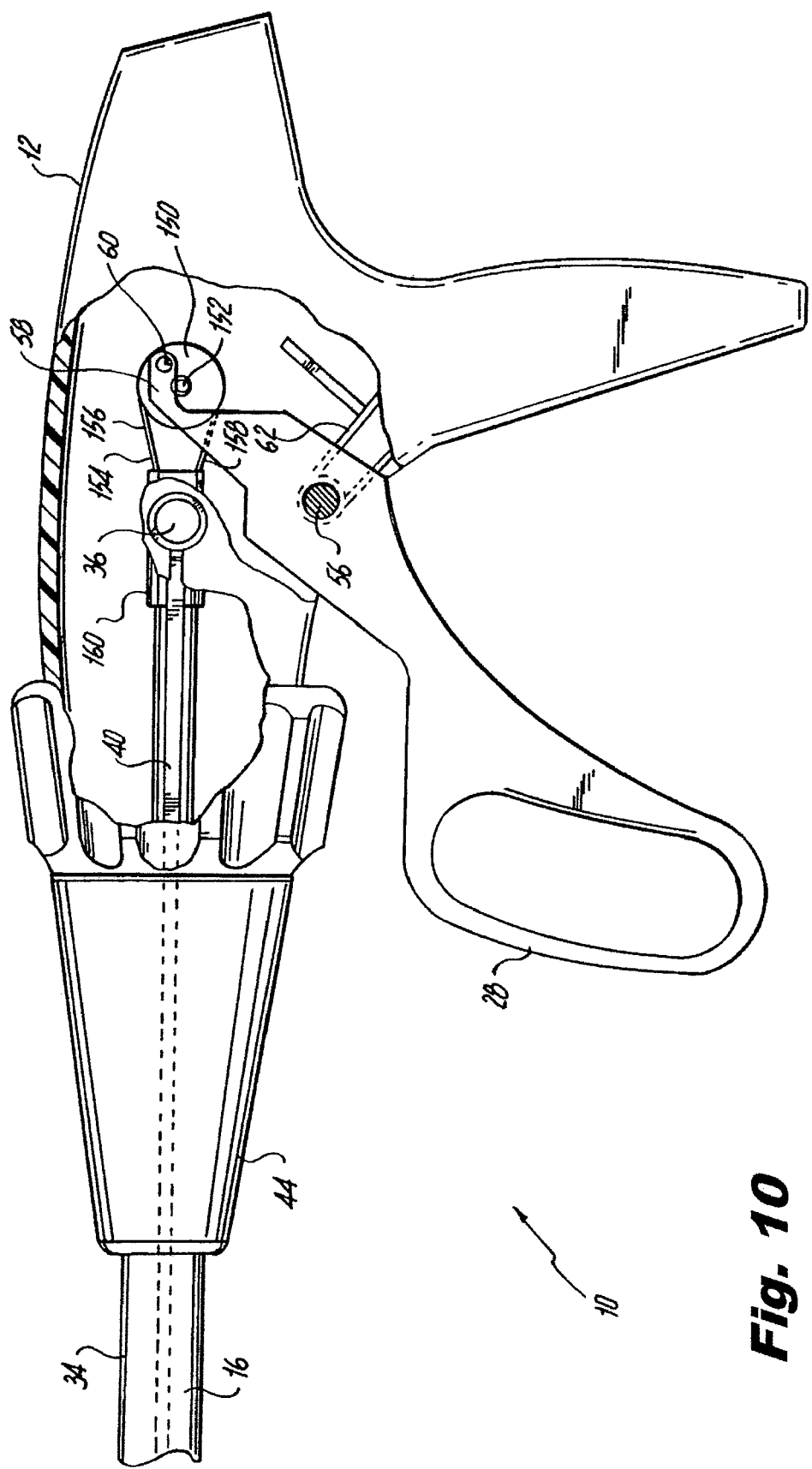
FIG. 10 is a side view, partially shown in section, of a handle assembly of a surgical stapler incorporating an alternative embodiment of a driving force mechanism.

Referring now to FIGS. 10-14, and initially with reference to FIGS. 10 and 11, in use, trigger 28 is in the unfired position with wheel 150 at rest. Proximal portion 34 of elongate tubular member 16 is in longitudinal alignment with articulation section 30 and distal portion 32. Anvil 26 is in the open position spaced apart from staple cartridge 24.

Figure 12:
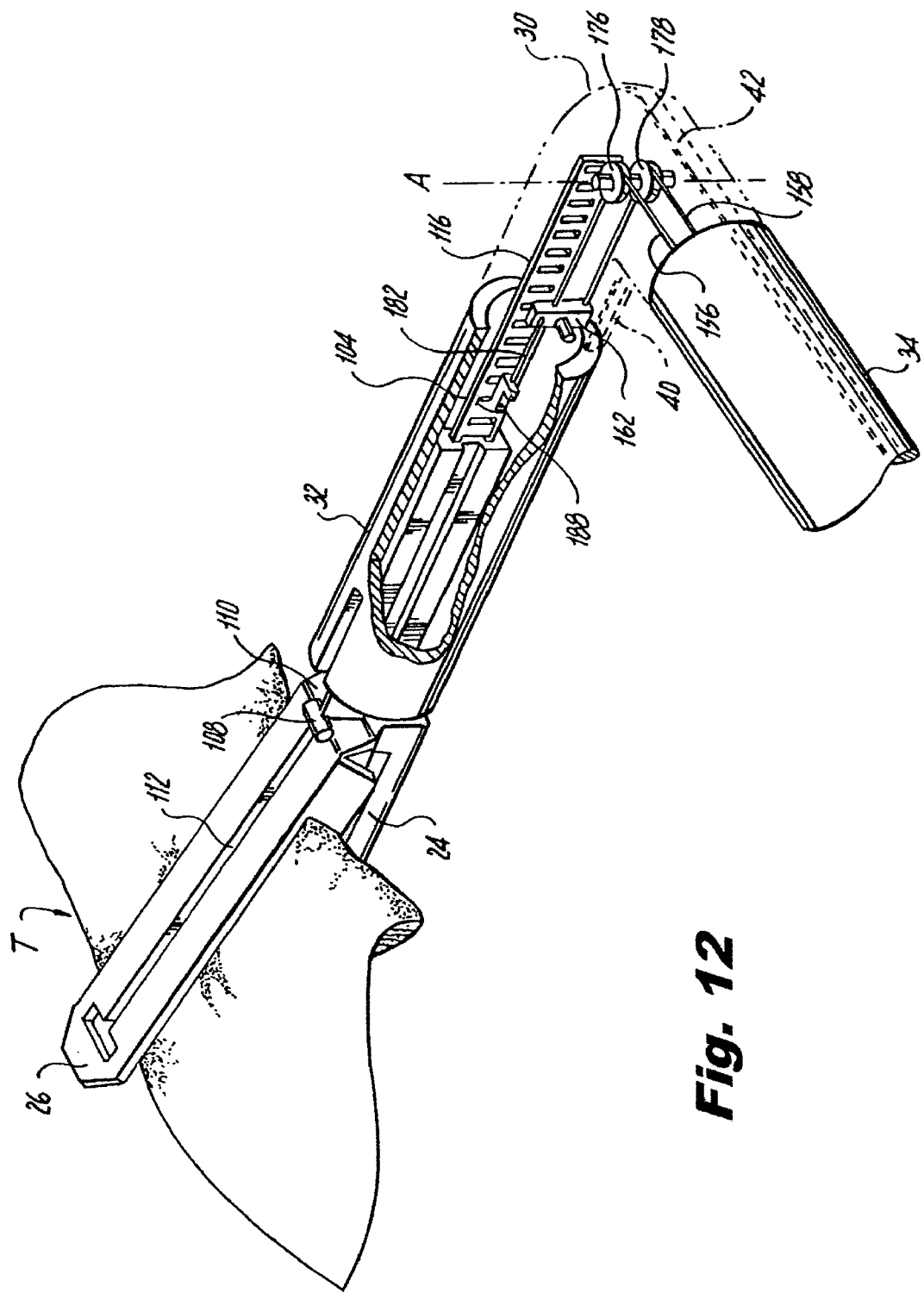
FIG. 12 is a perspective view, partially shown in section, of the distal end portion of the surgical stapler of FIG. 10, shown in an articulated position, positioned about tissue.

Referring to FIGS. 10 and 12, as discussed hereinabove, articulation actuator 36 is activated to bend elongate tubular member 16 at articulation section 30 and position jaw assembly 16 relative to a tissue section "T" such that anvil 26 and staple cartridge 24 are positioned about a tissue section T. Trigger 28 is activated to rotate wheel 150 clockwise drawing lower section 158 of drive cable 154 proximally and forcing or allowing upper section 156 to move distally.

As shown in FIG. 12, upper section 156 of drive cable 154 passes around upper wheel 176 in articulation section 30 while lower section 158 passes around lower wheel 178. As lower section 158 is drawn proximally, lower section 158 pulls on second end 174 of lever 162, rotating lever 162 clockwise and driving first end 170 of lever 162 distally.

Distal movement of first end 170 drives transfer bar 182 distally causing drive tooth 188 to engage a abutment 116 and advance actuator 104 distally within distal portion 32 of elongate tubular member 16.

Figures 13, 14:
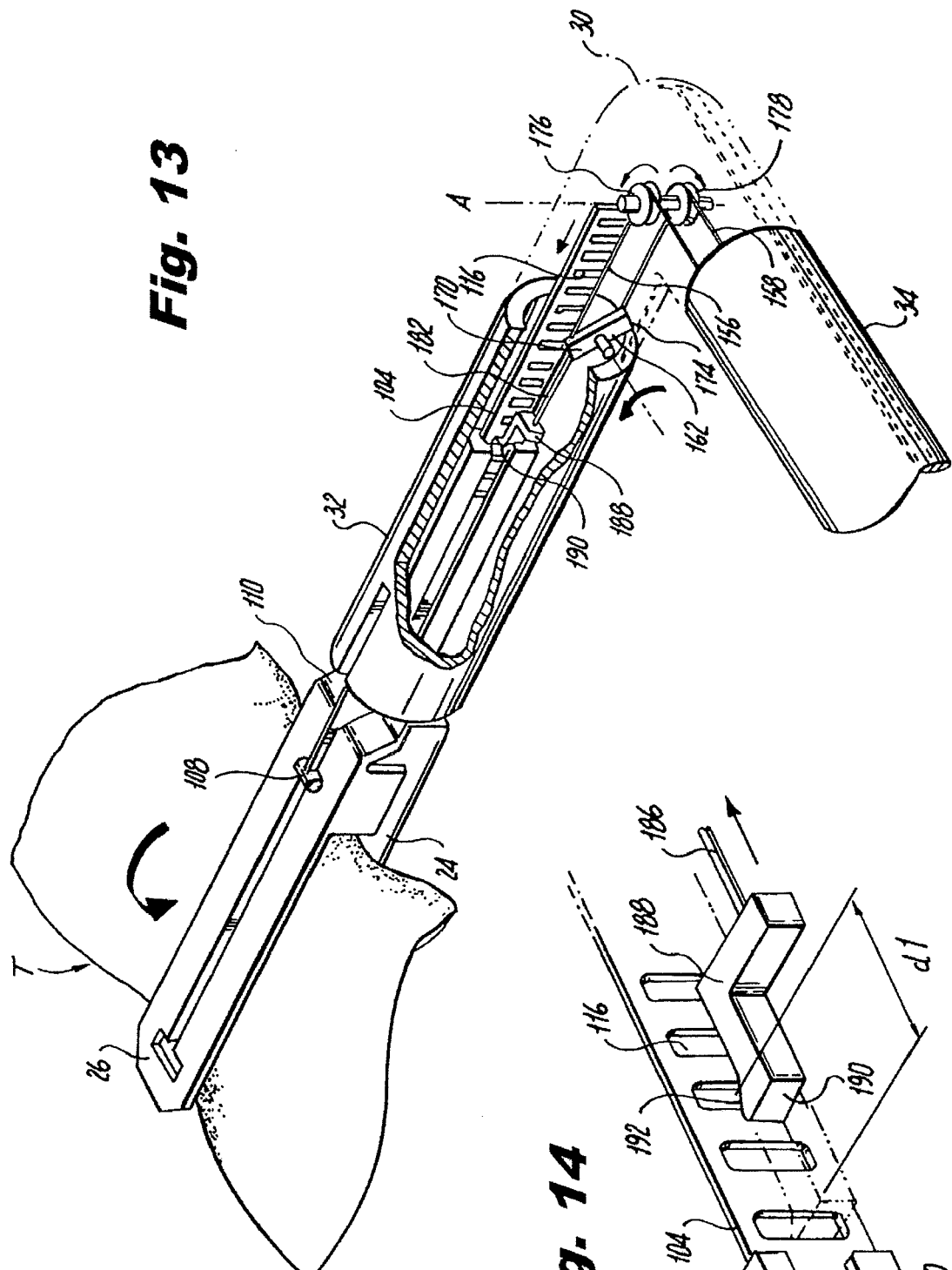
FIG. 13 is a perspective view similar to FIG. 12 during actuation.
FIG. 14 is an enlarged perspective view of a portion of the driving force mechanism resetting for a further actuation.

Referring to FIG. 13, and as discussed hereinabove, distal movement of actuator 104 forces crossbar 108 against angled edge 110 of anvil 26 to move anvil 26 to the closed position relative to staple cartridge 24. Subsequent activations of trigger 28 will result in further actuation of surgical stapler 10 to staple tissue T in the manner described hereinabove.

Referring to FIG. 14, drive tooth 188 also passes through stroke d1 to incrementally advance actuator 104 by successive engagements with abutments 116. Drive tooth 188 includes a distal drive face 190 for engagement with abutments and a proximal sloped face 192 which allows drive tooth 188 to disengage from a abutment 116 on a return stroke of drive tooth 188 and reengage a subsequent abutment 116.

In this manner the above described drive force mechanisms allow a driving force to be transmitted from a handle of the surgical instrument around an articulated section in the surgical instrument and, ultimately, transmitted to a jaw assembly of the surgical instrument.

It will be understood that various modifications may be made to the embodiments disclosed herein. For example, other activation mechanisms may be provided, such as, for example, gas powered, etc. Further, the disclosed driving force mechanisms are equally suited for use in surgical instruments having articulation point at or close to associated end effectors. Therefore, the above description should not be construed as limiting, but merely as exemplifications of particular embodiments. Those skilled in the art will envision other modifications within the scope and spirit of the claims appended hereto.

The invention claimed is:

1. A surgical instrument comprising:
   a handle having an elongate tubular member extending distally from the handle, the elongate tubular member having a proximal portion defining a longitudinal axis, a distal portion, and an articulation portion positioned between the distal and proximal portions to enable the distal portion to move through a plurality of angles relative to the longitudinal axis; and
   a drive force mechanism including a drive element positioned in the proximal portion, a transfer device positioned in the articulation portion, and a transfer bar positioned in the distal portion, the drive element directing a drive force through the proximal portion, the transfer device redirecting the drive force through the articulation portion, and the transfer bar receiving the driving force when the distal portion is positioned in at least one of the plurality of angles.

2. The surgical instrument as recited in claim 1, wherein the transfer device is a gear rotatably mounted at a point of articulation.

3. The surgical instrument as recited in claim 2, wherein the drive element includes a rack engagable with the gear so as to rotate the gear in response to longitudinal motion of the rack.

4. The surgical instrument as recited in claim 2, wherein the transfer bar includes a rack engagable with the gear such that rotation of the gear moves the transfer bar longitudinally within the distal portion.

5. The surgical instrument as recited in claim 1, wherein the transfer device includes at least one wheel rotatably mounted in the articulation portion.

6. The surgical instrument as recited in claim 5, wherein the drive element is a flexible cable, the flexible cable passing around the at least one wheel.

7. The surgical instrument as recited in claim 6, wherein the drive mechanism includes a rotating member rotatably mounted in the distal portion, a first end of the rotating member being connected to the transfer bar.

8. The surgical instrument as recited in claim 7, wherein the rotating member is selected from the group consisting of a lever, link and pawl.

9. The surgical instrument as recited in claim 7, wherein a second end of the rotating member is connected to the cable.

10. The surgical instrument as recited in claim 9, wherein the cable has an upper section and a lower section, the upper section being connected to the first end of the rotating member and the lower section being connected to the second end of the rotating member.

11. The surgical instrument as recited in claim 1, wherein the surgical instrument includes an actuator positioned in the distal portion to operate an end effector associated with the surgical instrument and the transfer bar is engagable with the actuator.

12. The surgical instrument as recited in claim 11, wherein the transfer bar includes a drive tooth engagable with the actuator.

13. The surgical instrument as recited in claim 12, wherein the drive tooth is releasably engagable with the actuator.

14. The surgical instrument as recited in claim 13, wherein the actuator includes a plurality of abutments and the drive tooth includes a drive face engagable within the abutments.

15. The surgical instrument as recited in claim 14, wherein the abutments are selected form the group consisting of windows, notches, pins and teeth.

16. The surgical instrument as recited in claim 14, wherein the drive tooth includes a proximal sloped face, the proximal sloped face engagable with the abutments to disengage the drive tooth from the abutments.

17. The surgical instrument as recited in claim 1, wherein the drive force is a firing force that facilitates the firing of the surgical instrument.

18. A surgical instrument comprising:
   a handle having an elongate tubular member extending distally from the handle, the elongate tubular member having a proximal portion, a distal portion and an articulation portion positioned between the distal and proximal portions, the articulation portion allowing the distal portion to move relative to the proximal portion;
   an end effector operatively coupled to the distal portion; and
   a drive force mechanism including a drive element positioned in the proximal portion, a transfer bar and an actuator positioned in the distal portion, the transfer bar being operatively coupled to the actuator, and a transfer device positioned in the articulation portion, the transfer device receiving a driving force from the drive element and reorienting the driving force around the articulation portion and to the transfer bar thereby actuating the end effector with the actuator.

19. The surgical instrument of claim 18, wherein the transfer bar is engagable with a plurality of abutments defined within the actuator to actuate the end effector upon the reception of the driving force.

20. The surgical instrument of claim 19, wherein the transfer bar is sequentially engagable with the plurality of abutments to ratchet the actuator and sequentially actuate the end effector.

* * * * *